(12) United States Patent
Tomlinson

(10) Patent No.: US 7,806,902 B2
(45) Date of Patent: Oct. 5, 2010

(54) SELF-ADJUSTING PRESSURE APPLICATOR

(76) Inventor: David R. Tomlinson, 38 Beech Tree Pl., Wakefield, RI (US) 02879

( * ) Notice: Subject to any disclaimer, the term of this patent is extended or adjusted under 35 U.S.C. 154(b) by 271 days.

(21) Appl. No.: 11/768,808

(22) Filed: Jun. 26, 2007

(65) Prior Publication Data

US 2008/0004654 A1    Jan. 3, 2008

Related U.S. Application Data

(60) Provisional application No. 60/816,798, filed on Jun. 26, 2006.

(51) Int. Cl.
 *A61B 17/32* (2006.01)
(52) U.S. Cl. .......................... 606/118; 24/522
(58) Field of Classification Search ................ 606/118, 606/120, 157, 131, 205, 207, 208; 227/180.1; 24/522, 528
See application file for complete search history.

(56) References Cited

U.S. PATENT DOCUMENTS

| | | | |
|---|---|---|---|
| 1,765,319 A | 6/1930 | Williams | |
| 2,272,072 A | 2/1942 | Ross | |
| 2,296,594 A * | 9/1942 | Blais et al. | .................. 606/118 |
| 2,353,647 A | 7/1944 | Carmichael | |
| 2,688,969 A | 9/1954 | Livoti | |
| 3,056,407 A | 10/1962 | Kariher et al. | |
| 3,072,126 A | 1/1963 | Fenton | |
| 3,392,728 A | 7/1968 | Bone et al. | |
| 3,473,533 A | 10/1969 | Freda | |
| 3,732,869 A | 5/1973 | Bronstein | |
| 3,757,787 A | 9/1973 | Gottlieb | |
| 5,163,943 A | 11/1992 | Mohiuddin et al. | |
| 5,309,641 A * | 5/1994 | Wonderley et al. | ............ 30/339 |
| 5,797,921 A | 8/1998 | Cimini et al. | |
| 6,193,129 B1 | 2/2001 | Bittner et al. | |
| 6,660,012 B2 | 12/2003 | Lahiji | |
| 6,780,194 B2 | 8/2004 | Freedman et al. | |
| 2004/0215210 A1 | 10/2004 | Duel | |
| 2006/0058814 A1 | 3/2006 | Gillis | |
| 2006/0122626 A1 | 6/2006 | Duel | |
| 2006/0219753 A1 | 10/2006 | Chiu et al. | |

* cited by examiner

*Primary Examiner*—(Jackie) Tan-Uyen T Ho
*Assistant Examiner*—Jonathan W Miles
(74) *Attorney, Agent, or Firm*—Peter J. Borghetti

(57) ABSTRACT

A self adjusting pressure applicator that can be used to retain tissue without causing injury to the tissue and that allows for repositioning of the retained tissue. Such a device can be used in conjunction with a circumcision clamp or other surgical instrument to ensure accurate positioning of the tissue prior to surgical manipulation. When used with a circumcision clamp such a device can ensure accurate removal of the desired amount of tissue resulting in improved surgical outcomes.

5 Claims, 7 Drawing Sheets

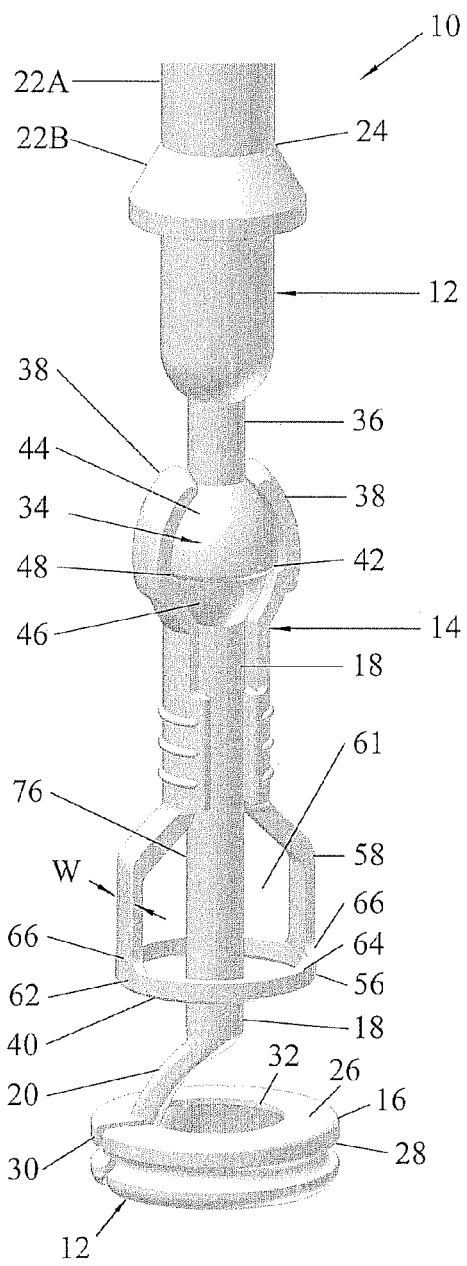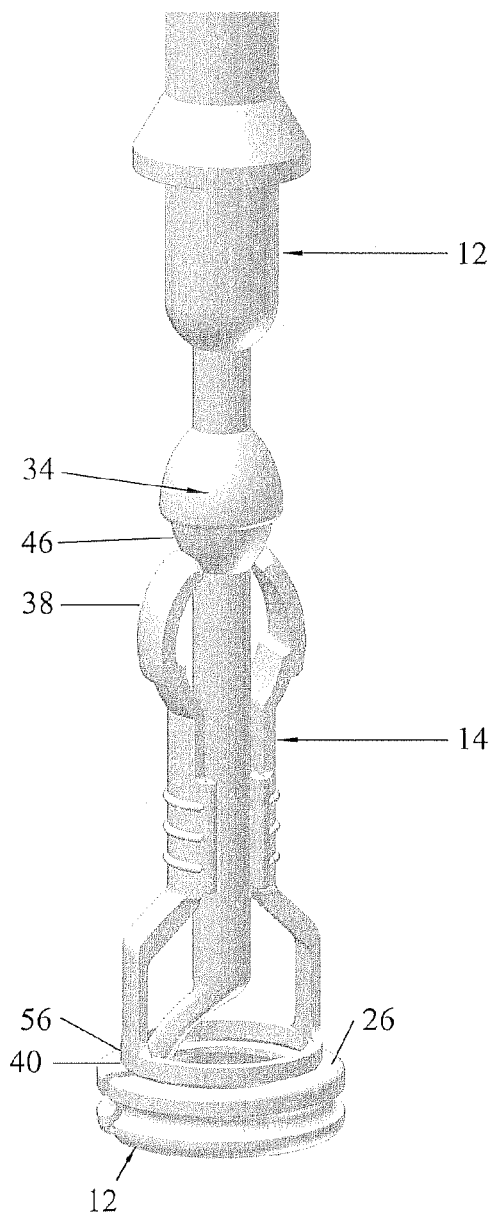
FIG 1A
FIG 1B

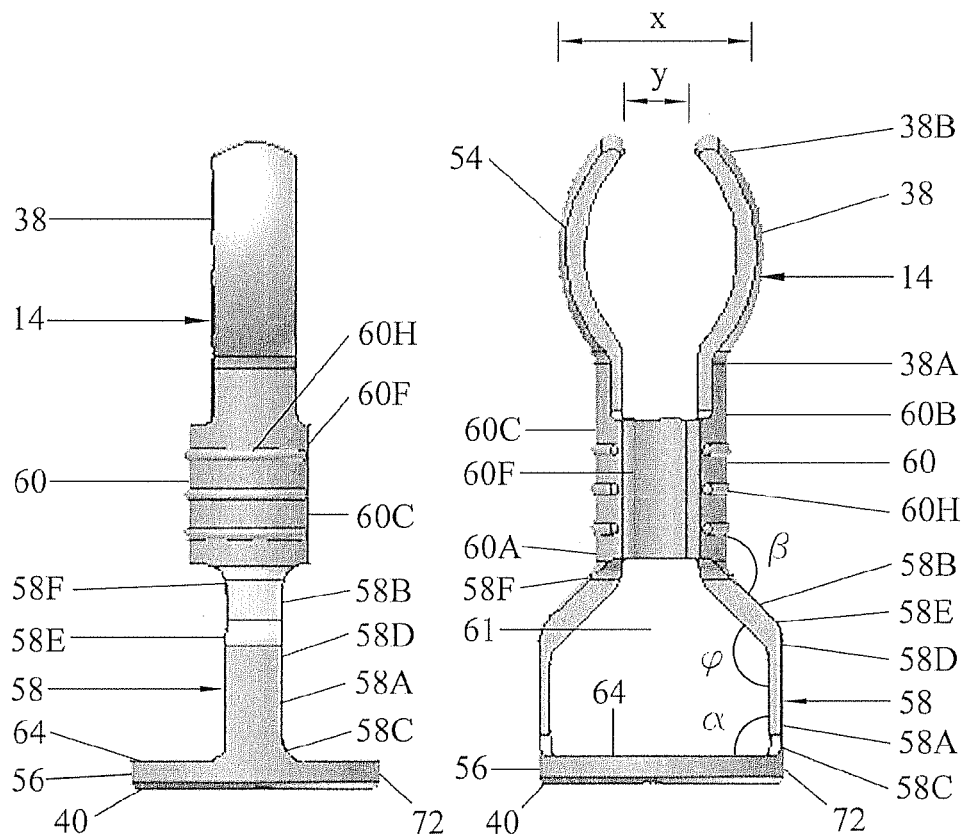
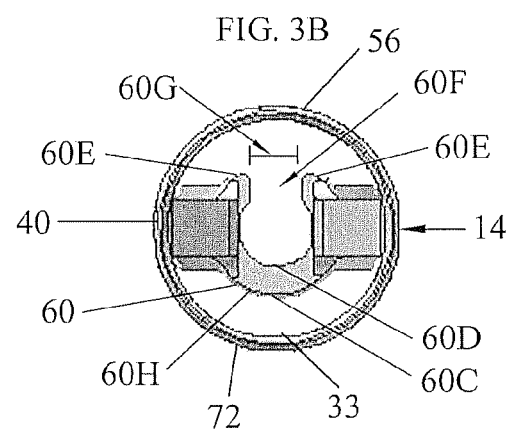
FIG. 3A  FIG. 3B
FIG. 3C

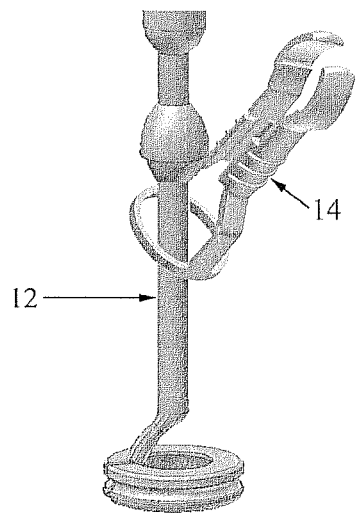 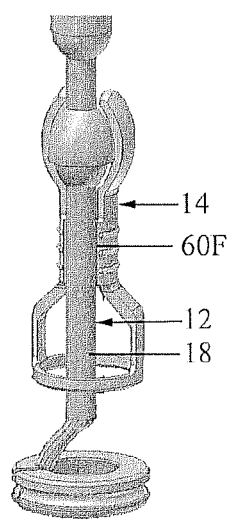 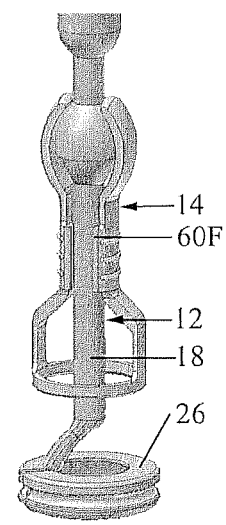
FIG. 4A  FIG. 4B  FIG. 4C
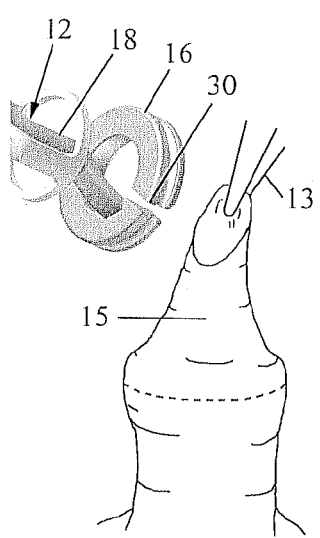 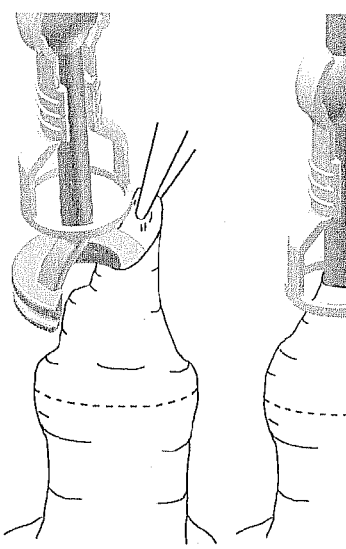 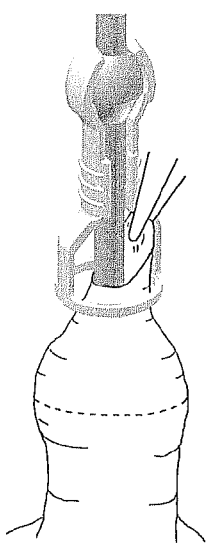 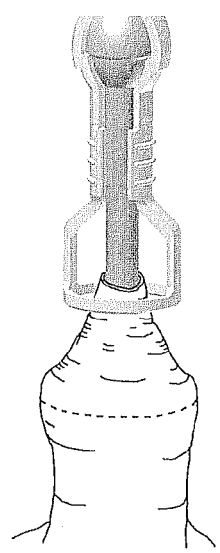
FIG. 5  FIG. 6  FIG. 7  FIG. 8

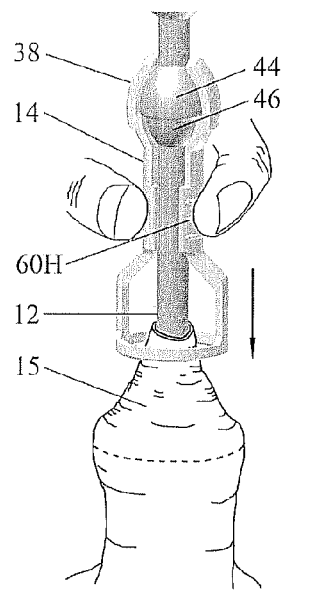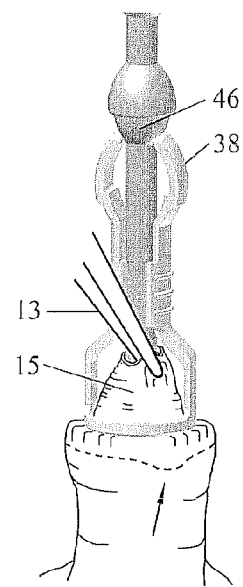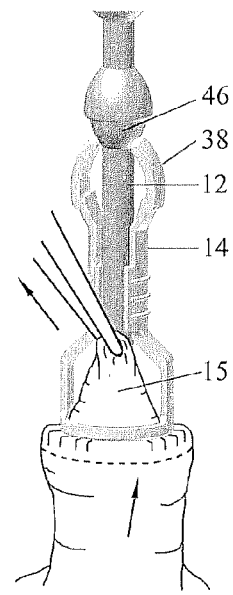
FIG 9A  FIG 9B  FIG 9C
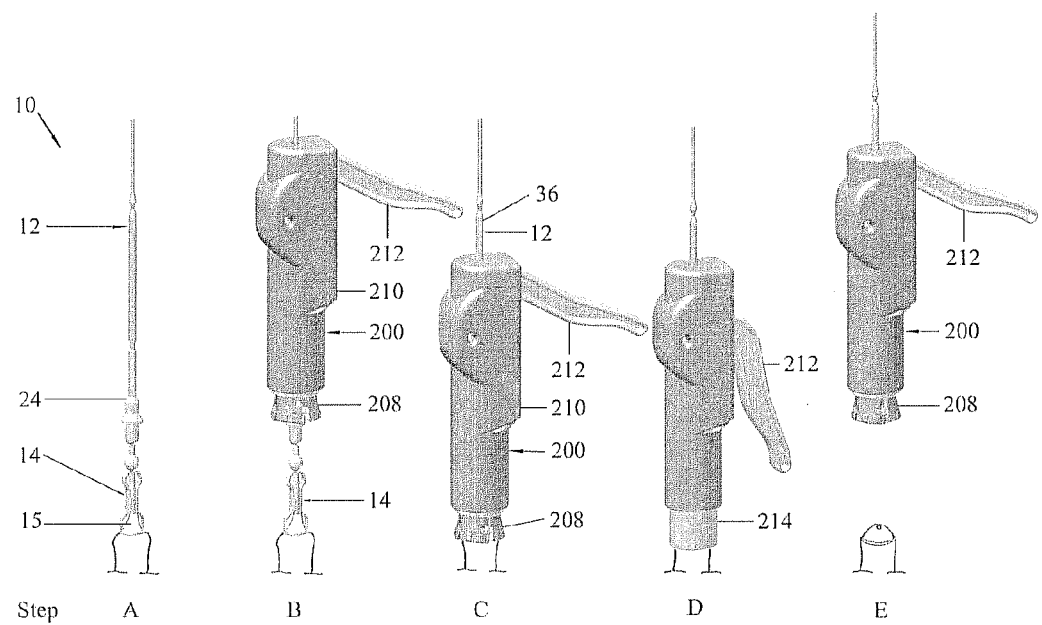
Step  A  B  C  D  E
FIG. 10

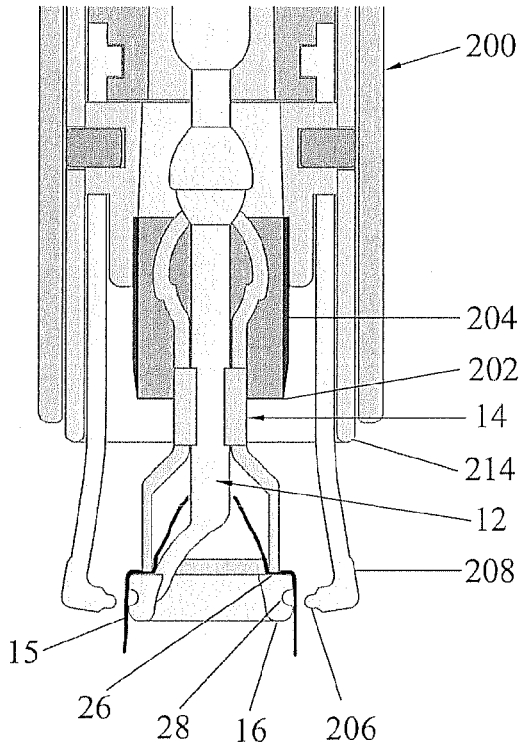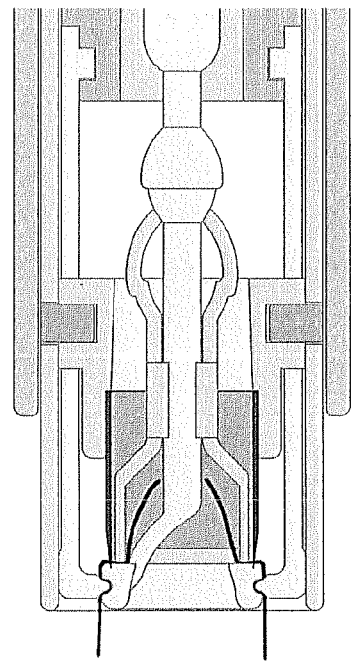
FIG. 11A  FIG 11B
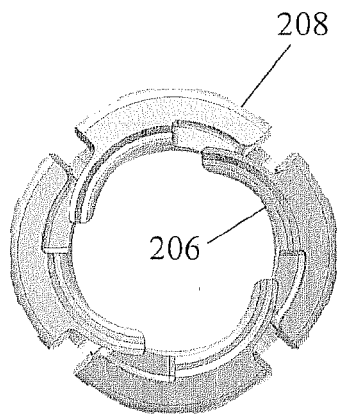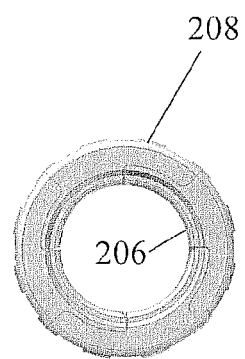
FIG 11C  FIG 11D

SELF-ADJUSTING PRESSURE APPLICATOR

CROSS REFERENCE TO RELATED APPLICATIONS

The present invention claims benefit of U.S. Provisional Application Ser. No. 60/816,798, entitled "SELF-ADJUSTING PRESSURE APPLICATOR" filed on Jun. 26, 2006, which is incorporated herein.

FIELD OF THE INVENTION

One embodiment of the present invention is related generally to the field of skin or tissue retention, and more particularly to a device for holding foreskin prior to the crushing and cutting associated with circumcision or other surgical procedures.

BACKGROUND OF THE INVENTION

Newborn circumcision is the most commonly performed surgical procedure in the World with an estimated 5 million circumcisions performed annually. Adult circumcisions are also performed routinely around the world. Circumcision has been performed for centuries for both religious and medical reasons. Circumcision instruments should, among other characteristics, provide a repeatable and a consistent level of hemostasis to help control bleeding and provide a method to safely and accurately incise the desired amount of foreskin tissue.

SUMMARY OF THE INVENTION

According to the invention, there is provided a self-adjusting pressure applicator, as defined in claims 1-19.

For a better understanding of the present invention, together with other and further objects thereof, reference is made to the accompanying drawings and detailed description.

BRIEF DESCRIPTION OF THE DRAWINGS

The present invention is illustratively shown and described in reference to the accompanying drawings, in which:

FIG. 1A is a perspective view of one embodiment of the present invention shown in the up position or disengaged;

FIG. 1B is a perspective view of one embodiment of the present invention shown in the down or engaged position;

FIGS. 3A-B are side views of the foreskin holder of FIG. 2;

FIG. 3C is a bottom view of the foreskin holder of FIG. 2;

FIGS. 4A-C illustrate the assembly of the foreskin holder of FIG. 2 on to an exemplary embodiment of the ring component;

FIGS. 5, 6, 7, and 8 are pictorial views of the ring component being inserted into the foreskin of a penis;

FIGS. 9A-C illustrate the positioning of foreskin between the foreskin holder and the ring component of FIGS. 4A-C;

FIG. 10 are pictorial views illustrating use of the present invention with a clamping-cutting device;

FIG. 11A illustrates a cross section of the foreskin being held in position by the present invention prior to clamping and cutting by the clamping-cutting device of FIG. 10;

FIG. 11B illustrates a cross section in the crushing and cutting position.

FIG. 11C demonstrates a bottom view of just the retractable arms in the open, neutral position.

FIG. 11D demonstrates a bottom view of just the retractable arms in the closed, clamping position.

DETAILED DESCRIPTION OF THE INVENTION

Figure 2:
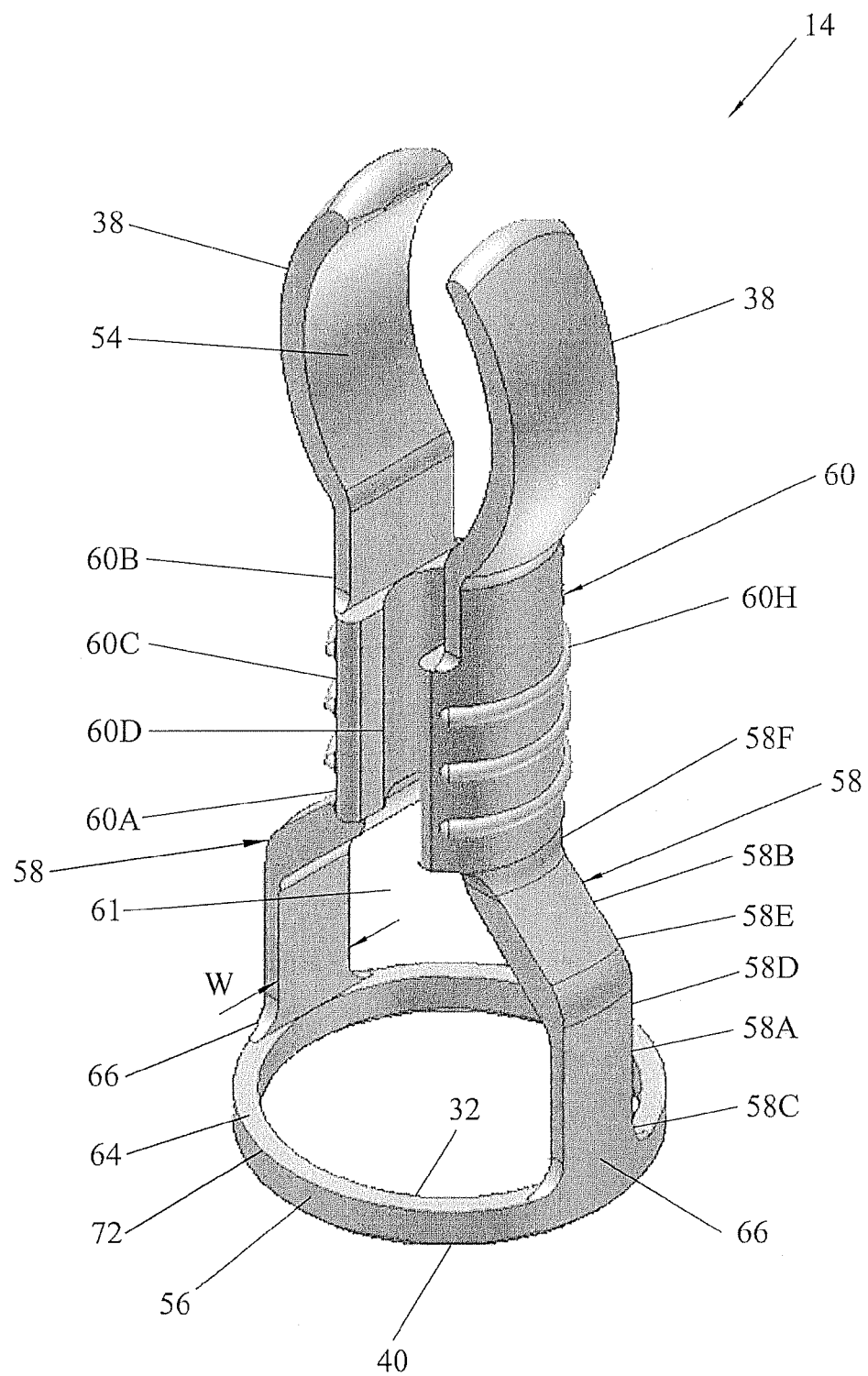
FIG. 2 is a perspective view of an exemplary foreskin holder of the present invention of FIG. 1.

The following disclosure of the present invention illustrates the self-adjusting pressure applicator adapted for use with a circumcision tool. However, it is contemplated within the scope of the invention for uses on any tissue such as brain or neuron tissue or cardiac vessel, as well as foreskin. Therefore, the invention should not be limited to use with only a circumcision tool as disclosed.

One embodiment of the present invention 10, illustrated in FIGS. 1A and 1B, includes ring component 12 and foreskin holder 14. FIGS. 1A and 1B illustrate ring component 12 and foreskin holder 14 in the disengaged and engaged positions, respectively. Ring component 12 is a single, one-piece, solid member made from, for example, injection molding of a malleable, elastic material (such as plastic) with an open ring 16 mounted orthogonally to lower shaft 18 by curved member 20, which allows manipulation of ring 16 within the foreskin. Ring component 12 includes a position adjustor 34 that delineates the lower shaft 18 from the upper shaft 36. Ring 16 can include an opening or gap 30 large enough to allow the thickness of the foreskin to enter. Ring 16 can include an inner diameter 32 large enough to receive a predetermined sized glans and shield the glans or head of the penis from being clamped and/or cut. Lower Shaft 18 (not shown) and/or upper shaft 36 (shown) can include a plurality of diameters 22A, 22B to control the insertion of ring component 12 into a clamping-cutting device 200 (disclosed in PCT international application PCT/US2005/022404 and incorporated herein by reference). A shaft diameter change can be delineated by a notch or ledge or, as illustrated in FIG. 1A, shoulder 24 that acts as a stop of ring component 12 into clamping-cutting device 200 (see FIG. 10).

Now turning to FIGS. 11A-D, ring 16 includes a holding/cutting surface 26 on its top surface being adapted to act as a holding surface when foreskin holder 14 is engaged and a cutting surface when cutting edge 202 of blade 204 of clamping-cutting device 200 is pressed down against foreskin 15 interposed between holding/cutting surface 26 and cutting edge 202. Ring 16 may also include grooved outer surface 28 adapted to engage with inward radial extension 206 of retractable arm 208 to hold ring component 12 in a stationary position relative to clamping-cutting device 200 (See FIG. 11) during the clamping/cutting operation, such that the foreskin 15 is trapped between the grooved outer surface 28 and the radial extension 206 of the retractable arms 208 (See FIG. 11). Grooved outer surface 28 will interact with inward radial extension 206 to crush the foreskin against grooved outer surface 28 and contemporaneously hold ring component 12 in position while circular blade 204 is delivered to make the incision in the foreskin.

Now returning to FIGS. 1A and 1B, one example of the present invention illustrates position adjustor 34 that cooperates with malleable, spring-like opposing arms 38 of foreskin holder 14 to apply a hands-free self-adjusting constant pressure force upon the foreskin disposed between lower surface 40 of foreskin holder 14 (FIGS. 1A and B) and holding/cutting surface 26 of ring component 12. Malleable arms 38 and position adjustor 34 act as pressure force generators. This arrangement provides for flexibility in positioning the foreskin prior to cutting while maintaining a predetermined pressure force. One embodiment for the present invention applies a pressure force between 50 and 200 grams to the tissue when engaged. Another embodiment applies a pressure force of about 181 grams of force to the tissue when engaged. The pressure force is exerted along a common centerline of ring component 12 and foreskin holder 14.

One embodiment of the present invention is engaged only long enough to insert the present invention 10 into the clamp, activate the clamp or otherwise cut the foreskin, thereby removing the retained foreskin from the patient. For example, the present invention can be engaged ranging from about 30 seconds to about one minute, the foreskin can be positioned between the two components, the clamp applied, and the retained foreskin crushed and excised. The agility, flexibility, and simplicity of the present invention allows for repositioning of the foreskin to assure substantially full or entire circumferential retention of the foreskin or tissue. Such minor adjustments can be made with great precision within a short period of time and with no tissue damage. Providing full circumferential retention of the foreskin or tissue along the crushing and cutting surface results in an improvement of the surgical removal of the foreskin or tissue without the use of barbs, pins, clips, or hemostats.

Another embodiment of the present invention applies the pressure force indefinitely to the tissue being retained allowing for prolonged surgical manipulation of that tissue without causing permanent injury.

One embodiment of position adjustor 34 is generally a circular body, having a tapered surface, and can be, for example, in the form of two unequal half spheres (similar to football halves) that create a shoulder or lip 42 when joined together. An upper half sphere 44 can have a diameter at the joining interface 48 larger then the mating diameter of lower half sphere 46. Spheres 44, 46 each have a tapered surface to facilitate the upward and downward movement of malleable arms 38 on the spheres 44, 46. The shoulder 42 formed at interface 48 acts as a malleable arm stop to inhibit the upward progress of malleable arms 38 as the foreskin is pulled upward to position it for crushing and cutting. The malleable arms 38 must be spread open to fit over shoulder 42 and into the disengaged position. The concave configuration of malleable arms 38 can be sized and shaped to spheres 44, 46 for containment of the foreskin holder 14 while in the disengaged position (FIG. 1A) and for spring-back properties while in the engaged position (FIG. 1B). The tapered surface of lower sphere 46 can be sized and shaped to provide the desired predetermined pressure force taking into consideration the spring-back force of malleable arms 38. Malleable arms 38 must always be in contact with lower sphere 46 to maintain a constant predetermined pressure on to the foreskin when foreskin is disposed between lower surface 40 of foreskin holder 14 and holding/cutting surface 26 of the ring component 12.

In furtherance of the description to hold foreskin in a precise location, when the foreskin holder 14 is positioned in the down or engaged position, malleable arms 38 of the foreskin holder 14 interact with the lower tapered surface 46 of position adjustor 34 forming a spring-like mechanism to create a force in the direction towards holding/cutting surface 16 and away from position adjustor 34. The spring-like mechanism exerts a force that holds foreskin holder 14 in place along the holding/cutting surface 26 of ring component 12. The pressure force in turn holds the foreskin in place that is positioned between the holding/cutting surface 26 and the foreskin holder ring portion 56. Ring portion 56 at the base of the foreskin holder 14 applies a 360° circumferential force to the holding/cutting surface 26 to achieve a substantially constant circumferential pressure or holding force. Shoulder 42 of the position adjustor 34 along interface 48 acts as a latch allowing for malleable arms 38 to move down lower shaft 18, but prevents inadvertent movement of foreskin holder 14 back up into the disengaged position. Shoulder 42 ensures that malleable arms 38 and lower tapered surface 46 maintain in an axial position that generates the spring-like force holding the foreskin holder 14 in place relative to holding/cutting surface 26 of ring component 12. Ring portion 56 of foreskin holder 14 is preferably supported by two support arms 58 (discussed in detail below) that allow for easy visibility and access to the foreskin that becomes retained within the cavity 61 of foreskin holder 14.

Now turning to FIG. 2 for a complete discussion of foreskin holder 14. One example of the foreskin holder 14 is a single, one-piece, injected molded, solid member constructed of malleable, elastic material (such as plastic). As mentioned above, foreskin holder 14 includes a ring portion 56, a pair of support arms 58, a C-shaped sleeve 60, and a pair of malleable arms 38. Ring portion 56 is configured to align juxtaposition to the holding/cutting surface 26 of ring 16 (see FIG. 1A) of the ring component 12. Ring portion 56 is general circular with an inner diameter 32, outer diameter 72, a bottom surface 40, and a top surface 64. Bottom surface 40 is a pressure surface that contacts and applies pressure to the foreskin disposed between the holding/cutting surface 26 of the ring component 12.

As discussed above, malleable arms 38 will exert a downward force caused by its interaction with a position adjustor 34 on the modified ring component 12. The spring coefficient of the malleable arms 38 can be derived by well known methods to accommodate the desired pressure force. The desired pressure force can be determined by knowing, among other characteristics, thickness of tissues including but not limited to foreskin, brain or neuron tissue, or cardiac vessel. The downward force is translated through C-shaped sleeve 60 to support arms 58. Supports arms 58 applies the translated force to ring portion 56 at interconnect points 66. The force will be substantially evenly distributed along lower surface 40 when lower surface 40 is in contact with foreskin disposed between lower surface 40 and holding/cutting surface 26 of the ring component 12. The force or contact pressure distribution along to lower surface 40 is a function of width W of support arms 58 and the rigidity of ring portion 56. For example, the wider the support arms 58, the more ring portion surface area in the direct load path of the translated force. Ring portion 56 would bend less when the ring portion 56 is more rigid. Bending of ring portion 56 could cause a reduction of the contact pressure along lower surface 40 as a function of circumferential distance from the interconnect points 66.

Though a pair of independently deflectable malleable arms have been used to illustrate a spring-like mechanism to apply a pressure force, it should be appreciated that there are many suitable combinations of arm (deflectable or rigid) or spring-like mechanisms incorporated into the body of the position adjustor 34 that will achieve the desired results. The invention should not be limited to only the embodiments disclosed in this application.

Now turning in FIGS. 3A-C, one embodiment of a support arm 58 can include one or more sections. Shown as an example is support arm 58 having two sections 58A, 58B. Two support arms 58 provides for easier visibility and access to the foreskin that becomes retained within the foreskin holder 14. Section 58A is attached at one of its ends 58C to either top surface 64 or to the inner diameter 33 (FIG. 3C) or to the outer diameter 72. One embodiment of Section 58A can be oriented orthogonal to ring portion 56. However any angle α (FIG. 3B) that applies evenly distributed forces along lower surface 40 of ring portion 56 is acceptable. Section 58B is attached at a predetermined angle Ø at one of its ends 58E to the other end 58D of section 58A, and at its other end 58F to C-shaped sleeve 60 at its end 60A at a predetermined angle β. The angular relationships between sections 58A and 58B and C-shaped sleeve 60 create an inward taper of support arms 58. The predetermined angles α, Ø, and β, and therefore the support arm taper, can be variable to accommodate the independent optimization of ring portion 56 and C-shaped sleeve 60, and/or to optimize the contact pressure along lower surface 40. In the case where Ø is 180°, there will only be one section 58. Though the preferred number of support arms is two, any number of support arms is acceptable and within the contemplation of the invention.

Continuing with the embodiment illustrated in FIG. 3B, each malleable arm 38 is attached at one of its ends 38A to end 60B of C-shaped sleeve 60 and its other end 38B is free to independently flex or deflect (X) and form a gap (Y) at rest. Free ends 38B can deflect to predetermined distance X under predetermined load or force conditions (discussed in detail below). The flexed or deflected malleable arms act like a spring storing energy to produce a spring back force, which is a function of the deflection distance X. The larger the deflection distance X, the more spring-back force will be created. Since the spring back force is also a function of the materials property, for example the modulus of elasticity, material selection is also important in determining the desired spring back force. It will become apparent later in this application that the spring back force will act upon a position adjustor 34 of ring component 12 to result in a downward movement of foreskin holder 14 that applies the pressure force to the foreskin disposed between lower surface 40 and holding/cutting surface 26 of ring component 12. Malleable arms 38 can be of any configuration that results in the desired spring back force working in conjunction with position adjustor 34 of ring component 12. For example, malleable arms 38 can have a concave surface 54 and be opposingly oriented to each other. As discussed above, the type of materials, dimensions (thickness, width, length) of malleable arms 38, and/or shape of malleable arms 38 (concave or convex) are derivable from the desired pressure force to be applied to a target tissue, such as foreskin, brain or neuro tissue, or cardiac vessel.

Now turning to FIG. 3C, C-shaped sleeve 60 in generally cylindrical in shape and hollow having an outer diameter 60C, an inner diameter 60D, and two circumferential ends 60E, which form slot 60F with gap 60G. Gap 60G is less than inner diameter 60D of C-shaped sleeve 60 and less than the outer diameter 76 of lower shaft 18 of ring component 12 (FIG. 1A). C-shape sleeve 60 has sufficient elastic properties such that gap 60G will open as lower shaft 18 is inserted through slot 60F and gap 60G will close or return to its original gap distance 60G after insertion of lower shaft 18 into slot 60F. Once lower shaft 18 is inserted through slot 60F, it is trapped or entrained within C-shaped sleeve 60 and only permitted to move along in a longitudinal path within C-shape sleeve 60 because outer diameter 76 is smaller than inner diameter 60D to allow for lower shaft 18 to move longitudinally within inner diameter 60D. Ends 60E can be rounded to facilitate easier insertion of lower shaft 18 through slot 60F. FIGS. 4A-C illustrate foreskin holder 14 (female component) being positioned on ring component 12 (male component) (FIG. 4A), alignment of slot 60F of foreskin holder 14 with lower shaft 18 of ring component 12 prior to insertion (FIG. 4B), and foreskin holder 14 slidably connected with ring component 12 after insertion of lower shaft 18 through slot 60F (FIG. 4C).

One embodiment of outer diameter 60C can include finger grips 60H to facilitate a better grip for raising and lowering foreskin holder 14 relative to ring component 12. Finger grips 60H can be one or more projections. As shown in FIGS. 3A and 3B, three projections 60H are circumferentially oriented parallel to each other along outer diameter 60C. Any cluster or grouping of projections are acceptable as well as any surface treatment that creates a frictional condition between the user's fingers and outer diameter 60C.

FIGS. 5, 6, 7, and 8 demonstrate an example of the insertion of ring 16 into the foreskin 15. As discussed above, gap 30 allows entry of ring 16 into foreskin 15. Foreskin 15 is held by an atraumatic forceps 13 while gap 30 is positioned to enter foreskin 15. With a pair of non-traumatic forceps, the foreskin is gently grasped and foreskin 15 is guided into the gap 30 of ring 16. With a screw-like motion of lower shaft 18 of ring component 12, the ring 16 is advanced in, down, and around the inner aspect of the foreskin 15. The gap 30 in ring 16 allows the ring 16 to be advanced into the foreskin with a smooth, non traumatic fluid screwing motion. Once ring 16 is fully inserted and resides just beneath foreskin 15, it can be pushed down slowly toward the glans to free any adhesions but to be surrounded by foreskin 15. Inside foreskin 15, gap 30 is closed by the elastic nature of the foreskin 15 attempting to return to its state after being stretched during the insertion of ring 16. The closed ring 16, inside the foreskin of the penis, residing just above the glans or tip of the penis, is then used as the compressive surface for any number of clamps, such as inward radial extension 206 (FIG. 11A), and its top surface 26 acts as a combination glans shield, cutting surface for blade 204 as it cuts the foreskin, and foreskin holder when cooperating with foreskin holder 14.

FIGS. 9A-C illustrate the operation of foreskin holder 14 after foreskin is positioned on the ring 16 of ring component 12 (hidden beneath foreskin 15). The operator pinches or grips finger grips 60H of foreskin holder 14 and pushes foreskin holder 14 down towards holding/cutting surface 26 (hidden beneath foreskin 15) (FIG. 9A). The dashed line represents the desired circular foreskin cutting circumference. Malleable arms 38 automatically open as malleable arms 38 move down upper sphere 44 and then automatically close as malleable arms 38 transition to move down lower sphere 46. The operator uses forceps 13 to grab the foreskin 15 for initial positioning for a substantially circular cut, shown as a dashed line (FIG. 9B). After initial positioning, the operator pulls the foreskin 15 substantially upwards (FIG. 9C). Foreskin holder 14 may advance upward on to lower sphere 46. As foreskin holder 14 advances upward the spring back force of malleable arms 38 increases and the downward pressure increases to counter the upward pull on the foreskin and to maintain a substantially constant circumferential pressure force onto the foreskin. Repositioning of the forceps may be necessary to assure the foreskin is evenly distributed around holding/cutting surface 26 of ring component 12 (hidden beneath foreskin 15) for a substantially circular cut (dashed line).

FIG. 10 illustrates one embodiment of the present invention 10 adapted for use with a circumcision clamping-cutting device 200 (disclosed in PCT international application PCT/US2005/022404 and incorporated herein by reference) adapted to cooperate with each other. Step A: Ring 16 (hidden beneath foreskin 15) of ring component 12 is inserted into the foreskin 15 of the penis, as discussed above. Step B: Clamping-cutting device 200 is set in the open position with lever arm 212 rotated up and retractable arms 208 extending fully through the bottom of housing 210 and sleeve 214. Step C: Clamping-cutting device 200 is inserted onto upper shaft 36 of ring component 12. Downward movement of clamping-cutting device 200 and housing 210 onto upper shaft 36 is stopped when shoulder 24 contacts bottom face of an internal thru hole (not shown). Step D: Lever arm 212 is activated downward to advance sleeve 214 downward over retractable arms 208 causing the clamping force and delivering the internal circular blade 204 (FIG. 11A) to the foreskin 15. Sleeve 214 moves downwardly over retractable arms 208 causing retractable arms 208 to radially close on to and to exert lateral compressive force against the foreskin 15. Turning to FIGS. 10 and 11A and B, retractable arms 208 exert sufficient lateral compressive force or clamping such that inward radial extensions 206 (FIG. 11A) of retractable arms 208 forces the foreskin 15 into grooved outer surface 28 of ring 16, thereby clamping the foreskin 15. As sleeve 214 is advanced even further over the ring 16, blade 204 is delivered to the top surface 64 of ring 16 and creates the circular incision into the foreskin 15 when ring 16 is positioned within clamping-cutting device 200 (FIG. 11B). Using the top surface 64 of ring 16 as the cutting surface that is held in place by the closed retractable arms 208, blade 204 makes a single, clean, circumferential incision on top surface 64 of ring 16, removing the excess foreskin 15. The clamp is left in place for a period of time ensuring adequate crushing and hemostasis. Step E (FIG. 10): Lever arm 212 is lifted upward and retractable arms 208 release ring component 12, lifting sleeve 214 of the clamping-cutting device 200 and lifting blade 204 back up into housing 210 and releasing ring 16. Ring component 12 with severed foreskin is permanently locked within housing (not shown) 210 to prevent inadvertent reuse of any of the components of the device. All components and byproducts of the operation are thrown away, thereby completing the circumcision.

FIGS. 11C and 11D show a bottom view of the clamping arms 208 with radial extensions 206 by themselves in the open, neutral position and the closed, clamping position, respectively.

Figure 12A:
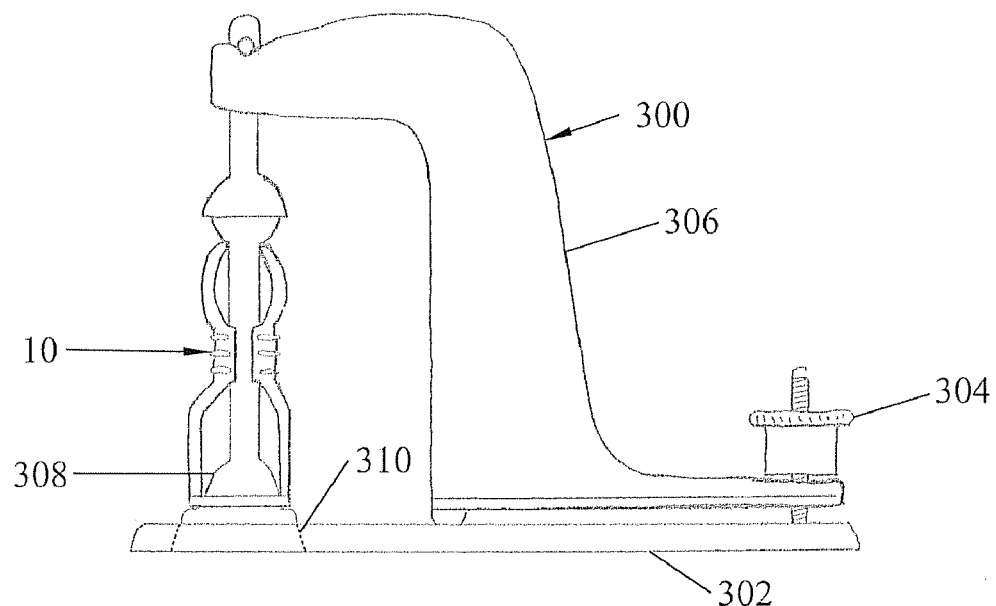
FIG. 12A is an illustration of the present invention of FIG. 1 adapted for use with a conventional circumcision clamp.

FIG. 12A illustrates the present invention 10 and a conventional type clamp 300, which includes plate 302, nut 304, yolk 306, and bell/stud 308, adapted to cooperate with each other.

Figure 12B:
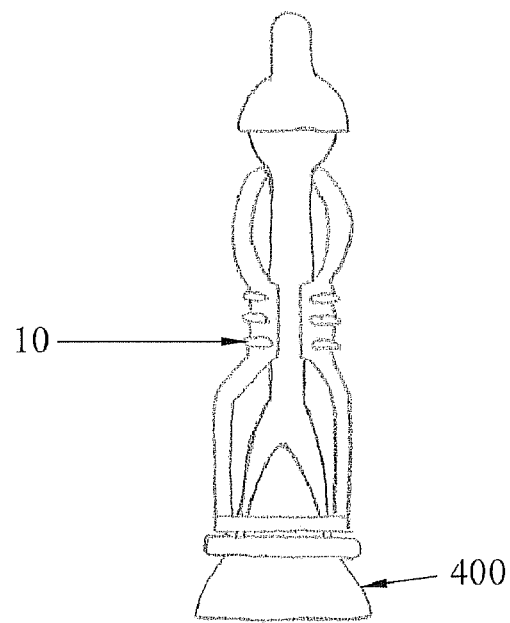
FIG. 12B is an illustration of the present invention of FIG. 1 adapted for use with a conventional circumcision bell.

FIG. 12B illustrates the present invention 10 and a conventional type bell 400 adapted to cooperate with each other Further embodiments of the above disclosed components are disclosed U.S. patent application Ser. No. 11/571,120 filed on Dec. 21, 2006, "Atraumatic Circumcision Device and Method to Use", by David R. Tomlinson, which is a U.S. national phase entry of Patent Cooperation Treaty international application serial number PCT/US2005/022404 filed on Jun. 23, 2005, "Atraumatic Circumcision Device and Method to Use", by David R. Tomlinson, which claims priority to U.S. provisional application Ser. No. 60/583,259 filed on Jun. 25, 2004, "Atraumatic Circumcision Ring and Method", by David R. Tomlinson, whereby all above listed applications are herein incorporated by reference.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A self-adjusting pressure applicator comprising:
   a monolithic ring component having a position adjustor that delineates a lower shaft from an upper shaft and a contact surface at an end of the lower shaft opposing the position adjuster;
      wherein the position adjustor comprises an upper half sphere having a larger diameter than an adjacent smaller diameter of a lower half sphere to form a shoulder;
      wherein the upper half sphere being directly connected to the upper shaft;
      wherein the lower half sphere being directly connected to the lower shaft; and
   a monolithic foreskin holder having a contact surface and a pair of opposing arms having deflectable free ends opposing the contact surface of the monolithic foreskin holder;
      wherein the pair of opposing arms automatically deflect outward as they move down the upper half sphere towards the lower half sphere and automatically retract inward as the pair of opposing arms move down the lower half sphere towards the contact surface of the monolithic ring component;
      wherein the shoulder prevents inadvertent movement of the pair of opposing arms of the monolithic foreskin holder up to the upper shaft opposing the contact surface of the monolithic ring component;
      wherein a spring back force is automatically generated by the pair of opposing arms in contact with the lower half sphere when a deflected gap between the free ends of the pair of opposing arms is greater than an initial gap to maintain a substantially constant circumference pressure force on to the tissue disposed between the contact surface of the monolithic ring component and the contact surface of the monolithic foreskin holder without the intervention of a user after a single axial sliding motion to position the pair of opposing arms in contact with the lower half sphere,
   whereby tissue disposed between the contact surface of the monolithic ring component and the contact surface of the monolithic foreskin holder is retained without causing injury to the tissue.

2. The applicator according to claim 1 wherein the substantially constant circumference pressure force ranges from about 50 to about 200 grams.

3. The applicator according to claim 1 wherein the monolithic ring component further comprises a shaft having an outer diameter and the monolithic foreskin holder further comprises a hollow cylindrical sleeve having an inner diameter, wherein the hollow cylindrical sleeve inner diameter is greater than the shaft outer diameter such that the monolithic ring component and monolithic foreskin holder are slidably movable along the common centerline.

4. The applicator according to claim 3 wherein the sleeve further comprises an outer diameter having at least one circumferential projection to form a grasping member, whereby a frictional condition is created between the user's fingers and outer diameter to allow for easy slideable movement of the second component relative to the first component.

5. The applicator according to claim 1 wherein the monolithic foreskin holder further comprises an outer diameter having at least one circumferential projection to form a grasping member, whereby a frictional condition is created between the user's fingers and outer diameter to allow for easy of slideable movement of the foreskin holder relative to the monolithic ring component.

* * * * *

UNITED STATES PATENT AND TRADEMARK OFFICE
Certificate

Patent No. 7,806,902 B2                                   Patented: October 5, 2012

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: David R. Tomlinson, Wakefield, RI (US); and Richard A. Dixon, Bountiful, UT (US).

Signed and Sealed this Second Day of October 2012.

S. THOMAS HUGHES
*Supervisory Patent Examiner*
Art Unit 3731
Technology Center 3700